(12) United States Patent
Meldgaard et al.

(10) Patent No.: US 11,542,294 B2
(45) Date of Patent: Jan. 3, 2023

(54) RAPID UNYLINKER CLEAVAGE (71) Applicant: Roche Innovation Center Copenhagen A/S, Horsholm (DK)

(72) Inventors: Michael Meldgaard, Hørsholm (DK); Marianne B. Mogensen, Hørsholm (DK); Dennis Jul Hansen, Hørsholm (DK)

(73) Assignee: Roche Innovation Center Copenhagen A/S, Horsholm (DK)

( * ) Notice: Subject to any disclaimer, the term of this patent is extended or adjusted under 35 U.S.C. 154(b) by 330 days.

(21) Appl. No.: 16/483,148

(22) PCT Filed: Mar. 22, 2018

(86) PCT No.: PCT/EP2018/057296
§ 371 (c)(1),
(2) Date: Aug. 2, 2019

(87) PCT Pub. No.: WO2018/177881
PCT Pub. Date: Oct. 4, 2018

(65) Prior Publication Data
US 2021/0292357 A1 Sep. 23, 2021

(30) Foreign Application Priority Data
Mar. 29, 2017 (EP) .................................. 17163501

(51) Int. Cl.
*C07H 21/00* (2006.01)
*C07H 1/00* (2006.01)
*C07H 1/06* (2006.01)

(52) U.S. Cl.
CPC ............... *C07H 21/00* (2013.01); *C07H 1/00* (2013.01); *C07H 1/06* (2013.01)

(58) Field of Classification Search
CPC .................................. C07H 21/00; C07H 1/00
See application file for complete search history.

(56) References Cited

U.S. PATENT DOCUMENTS 5,681,945 A * 10/1997 McLean ............... C07D 307/20
536/25.34
6,653,468 B1 * 11/2003 Guzaev .................. C07H 21/00
506/32

(Continued)

FOREIGN PATENT DOCUMENTS

WO WO 2005/049621 6/2005
WO WO 2005/061710 7/2005

(Continued)

OTHER PUBLICATIONS

McBride et al., "Amidine Protecting Groups for Oligonucleotide Synthesis" J Am Chem Soc vol. 108 pp. 2040-2048 (Year: 1986).*

(Continued)

*Primary Examiner* — Eric Olson
(74) *Attorney, Agent, or Firm* — Fish & Richardson P.C.

(57) ABSTRACT

Methods for cleaving oligonucleotides from a solid support are described as are methods for synthesizing an oligonucleotide on a solid support and subsequently cleaving the oligonucleotide from the solid support. In the methods, the 3' nucleoside of the oligonucleotide attached to the solid support is a LNA nucleoside. The method entail treating the bound oligonucleotide with a concentrated ammonium hydroxide solution for about 30 minutes to about 6 hours.

14 Claims, 3 Drawing Sheets

(56) References Cited

U.S. PATENT DOCUMENTS

2002/0143166 A1* 10/2002 Pires ............... C07H 21/00
　　　　　　　　　　　　　　　　　　　　　　　536/23.1
2015/0368288 A1　12/2015　Cedillo et al.

FOREIGN PATENT DOCUMENTS

| WO | WO 2007/031091 | 3/2007 |
| --- | --- | --- |
| WO | WO 2007/112754 | 10/2007 |
| WO | WO 2008/113832 | 9/2008 |
| WO | WO 2009/043353 | 4/2009 |
| WO | WO 2009/124238 | 10/2009 |
| WO | WO 2015/173208 | 11/2015 |
| WO | WO 2017/032726 | 3/2017 |

OTHER PUBLICATIONS

Moon et al., "Development of New Protecting Groups for Guanine Residue in Oligodeoxyribonucleotide Synthesis" Bull Korean Chem Soc vol. 12 No. 2 pp. 196-199 (Year: 1991).*

Seth et al., "Structure Activity Relationships of alpha-L-LNA Modified Phosphorothioate Gapmer Antisense Oligonucleotides in Animals" Molecular Therapy-Nucleic Acids vol. 1, e47, DOI:10.1038/mtna.2012.34 (Year: 2012).*

Kinovate, "NittoPhase®HL & NittoPhase® UnyLinker™ Solid Support" product overview, downloaded form www.kinovate.com (Year: 2015).*

Supporting information for Ravikumar et al., "Efficient and scaleable synthesis of Oligonucleotides utilizing a universal linker molecule. A novel approach to enhance the purity of drugs" Organic Process Research & Development 2008, 12, 399-410, downloaded from http://pubs.acs.org. (Year: 2008).*

Bergstrom "Unnatural Nucleosides with Unusual Base Pairing Properties," Current Protocols in Nucleic Acid Chemistry, 37:1.4.1.-1.4.32.

Capaldi and Scozzari, "Manufacturing and Analytical Processes for 2'-O-(2-Methoxyethyl)-Modified Oligonucleotides," Antisense Drug Technology: Principles, Strategies, and Applications, 2nd Edition, CRC Press, 2008, Chapter 14, pp. 401-434.

Guzaev and Manoharan, "A conformationally preorganized universal solid support for efficient oligonucleotide synthesis," J. Am. Chem. Soc., 2003, 125(9):2380-2381.

GlenResearch.com, "GlenUnysupport," Oct. 1, 2008, [retrieved on Jul. 31, 2019] retrieved from URL <http://www.glenresearch.com/GlenReports/GR20-25.html>, 20(2):16 pages.

Hirao et al., "Natural versus Artificial Creation of Base Pairs in DNA: Origin of Nucleobases from the Perspectives of Unnatural Base Pair Studies," Accounts of Chemical Research, Jan. 20, 2012, 45(12):2055-2065.

International Search Report and Written Opinion in International Application No. PCT/EP2018/057296, dated Jun. 14, 2018, 10 pages.

Ravikumar et al., "UnyLinker: An Efficient and Scaleable Synthesis of Oligonucleotides Utilizing a Universal Linker Molecule: A Novel Approach To Enhance the Purity of Drugs," Organic Process Research & Development, 2008, 12(3):399-410.

* cited by examiner

Figure 1:

| X=O: +337 | X=O: +354 | X=O: +278 | X=O: +261 |
| X=S: +353 | X=S: +370 | X=S: +294 | X=S: +277 |

RAPID UNYLINKER CLEAVAGE

CROSS-REFERENCE TO RELATED APPLICATIONS

This application is a U.S. national stage under 35 USC § 371 of International PCT Application Number PCT/EP2018/057296, filed on Mar. 22, 2018, which claims the benefit to European Patent Application Number 17163501.4, filed Mar. 29, 2017, which are hereby incorporated by reference in their entirety.

FIELD OF THE INVENTION

The present invention relates to the field of oligonucleotide synthesis using a solid support and in particular to the finding that when using a 3' oxy-LNA nucleoside attached to the solid support of the UnyLinker type, cleavage and deprotection occurs very rapidly.

BACKGROUND

Ravikumar et al., Organic Process Research & Development 2008, 12, 399-410, reports on the UnyLinker solid support for oligonucleotide synthesis and that cleavage and deprotection from the UnyLinker support is achieved in 8 hours at 55° C. (small scale synthesis). Guzaev and Manoharan, J. AM. CHEM. SOC. 2003, 125, 2380-2381, discloses that the kinetics of oligonucleotide cleavage from a solid support was 1-5-2.3 times faster for compounds bearing a 2'-O-alkylribonucleoside residue at the 3' terminus.

WO2005/049621 discloses 5,6-dihydroxy-isoindole derivatives as linkers for oligomer solid phase synthesis.

STATEMENT OF INVENTION

The invention provides a method for the cleavage of an oligonucleotide from a solid support, said method comprising the step (i) of treating the oligonucleotide bound to the solid support with a concentrated ammonium hydroxide solution for a period of at least about 30 minutes and no longer than about 6 hours, wherein the 3' nucleoside of the oligonucleotide attached to the solid support is a LNA nucleoside, which is covalently attached to the solid support at the 3' position as according to Formula I or II Formula I
beta-D-oxy
LNA Nucleoside Formula II
α-L-oxy
LNA Nucleoside wherein one of A' and A" is SM or L-SM, SM is a support medium;

L is a linking moiety, the other of A' and A" is H or a substituent;

each of $R_u$, $R_v$, $R_w$, $R_x$, $R_y$ and $R_z$ is H, alkyl, substituted alkyl, alkenyl, substituted alkenyl, alkynyl or substituted alkynyl;

$Y_1$ and $Y_2$ are each independently of one another O, S, $NR_1CH_2$ or $CR_1R_1$: $R_1$ is H, alkyl, substituted alkyl, alkenyl, substituted alkenyl, alkynyl or substituted alkynyl;

$G_1$ is O, S, or NR'; wherein R' is H or a substituent; X is O or S, $R^c$ is H or cyanoethyl;

wherein Base is a nucleobase, and $R^3$ is the remainder of the oligonucleotide.

In some embodiments each of $Y_1$ and $Y_2$ is O.

In some embodiments at least one of $Y_1$ and $Y_2$ is O.

In some embodiments A" is phenyl.

In some embodiments A" is L-SM.

In some embodiments A' is L-SM.

The invention provides a method for the cleavage of an oligonucleotide from a solid support, said method comprising the step (i) of treating the oligonucleotide bound to the solid support with a concentrated ammonium hydroxide solution for a period of at least about 30 minutes and no longer than about 6 hours, wherein the 3' nucleoside of the oligonucleotide attached to the solid support is a LNA nucleoside, which is covalently attached to the solid support at the 3' position as according to Formula I.

The invention provides for a method for the cleavage of an oligonucleotide from a solid support, said method comprising the step (i) of treating the oligonucleotide bound to the solid support with a concentrated ammonium hydroxide solution for a period of at least about 30 minutes and no longer than about 6 hours, wherein the 3' nucleoside of the oligonucleotide attached to the solid support is an LNA nucleoside, which is covalently attached to the solid support at the 3' position as according to formula A or C:

Formula A — beta-D-oxy LNA Nucleoside

Formula C — α-L-oxy LNA Nucleoside wherein the dark circle represents a solid support; $R^c$ is H or cyanoethyl, $R^e$ is aryl or $C_{1-10}$ alkyl, such as phenyl, isopropyl or methyl; wherein Base is a nucleobase, $R^3$ is the remainder of the oligonucleotide, and wherein X is O or S.

The invention provides for a method for the cleavage of an oligonucleotide from a solid support, said method comprising the step (i) of treating the oligonucleotide bound to the solid support with a concentrated ammonium hydroxide solution for a period of at least about 30 minutes and no longer than about 6 hours, wherein the 3' nucleoside of the oligonucleotide attached to the solid support is an LNA nucleoside, which is covalently attached to the solid support at the 3' position as according to formula A.

The invention provides a method of oligonucleotide synthesis comprising the step of cleavage of the oligonucleotide from a solid support as according to the method for the cleavage of an oligonucleotide from a solid support of the invention.

The invention provides for a method of oligonucleotide synthesis comprising the following sequential steps:
a) Provision of a solid support of Formula I or II, or Formula B or D Formula B — beta-D-oxy LNA Nucleoside Formula D — α-L-oxy LNA Nucleoside wherein the dark circle represents a solid support; $R^c$ is H or cyanoethyl, $R^e$ is aryl or $C_{1-10}$ alkyl, such as phenyl, isopropyl or methyl; wherein Base is a nucleobase, X is O or S, and Rz is a 5'-OH blocking group, such as a blocking group selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTrR$^b$, and CH—$R^a$—O-MMTrR$^b$, b) unblocking of the 5' group to provide a 5' terminal —OH group,
c) coupling a phosphoramidite monomer to the 5' terminal —OH group,
d) oxidizing the internucleoside linkage formed in the coupling step,
e) optionally capping any unreacted phosphoramidite5' terminal —OH group,
f) repeating steps b)-e) for one or more further cycles (chain elongation),
g) optionally carrying out an amine wash,
h) cleavage of the oligonucleotide from the solid support with a concentrated, ammonium hydroxide solution for a period of at least about 30 minutes and no longer than about 6 hours (or as according to the invention claimed or described herein),
i) optionally purifying the oligonucleotide.

DETAILED DESCRIPTION

Unless otherwise indicated the term about as used herein with reference to a numerical value may be +/−10% of the indicated integer (such as a temperature or time integer). As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl. Depending on the structure, an aryl group can be a monoradical or a diradical (i.e., an arylene group). In one aspect, an aryl is a $C_{6-10}$ aryl. In some embodiments aryl is phenyl. When substituted aryl may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group; or a group selected from the group consisting of halide, such as iodide, fluoride, bromide or chloride, such as phenyl substituted with halide, such as iodide, fluoride, bromide or chloride.

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, straight chain, or include a cyclic portion. The point of attachment of an alkyl is at a carbon atom that is not part of a ring. The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). Alkyl includes both branched and straight chain alkyl groups. The alkyl group of the compounds described herein may be designated as "$C_{1-6}$ alkyl" or similar designations. By way of example only, "$C_{1-6}$ alkyl" indicates that there are one, two, three, four, five, or six carbon atoms in the alkyl chain, i.e., the alkyl chain is selected from the group consisting of methyl, ethyl, propyl, iso-propyl, n-butyl, isobutyl, sec-butyl, and tert-butyl. Typical alkyl groups include, but are in no way limited to, methyl, ethyl, propyl, isopropyl, butyl, isobutyl, tertiary butyl, pentyl, hexyl, allyl, cyclopropylmethyl, cyclobutylmethyl, cyclopentylmethyl, cyclohexylmethyl, and the like. In one aspect, an alkyl is a $C_{1-6}$ or $C_{1-4}$ alkyl or $C_{1-3}$ alkyl. $C_{1-3}$ alkyl group means straight or branched alkyl group that has 1 to 3 carbon atoms. Examples of $C_{1-4}$ alkyl group are methyl, ethyl, propyl and isopropyl. $C_{1-3}$ alkyl group means straight or branched alkyl group that has 1 to 4 carbon atoms. Examples of $C_{1-3}$ alkyl groups are methyl, ethyl, propyl, isopropyl, butyl, isobutyl, and tert-butyl.

An "acyl protection group" comprises an acyl group —C(=O)—$R^7$, wherein $R^7$ is a terminal group, for example a group selected from, alkyl-, alkyl-, alkenyl-, alkynyl-, cycloalkyl- and aryl-group; or a group selected from, unsubstituted alkyl-, unsubstituted alkenyl-, unsubstituted alkynyl-, unsubstituted cycloalkyl- or unsubstituted aryl-group; or a group selected from substituted alkyl-, substituted alkenyl-, substituted alkynyl-, substituted cycloalkyl- or substituted aryl-group. In some embodiments $R^7$ may be selected from the group consisting of unsubstituted $C_{1-6}$-alkyl-, unsubstituted $C_{2-6}$-alkenyl-, unsubstituted $C_{2-6}$-alkinyl-, unsubstituted $C_{3-7}$-cycloalkyl- or unsubstituted phenyl-group or substituted $C_{1-6}$-alkyl-, substituted $C_{2-6}$-alkenyl-, substituted $C_{2-6}$-alkinyl-, substituted $C_{3-7}$-cycloalkyl- or substituted phenyl-group; wherein when substituted, the substituent group may be mono or poly substituted, e.g. with one or more substituents selected from the group consisting of halogen, $C_{1-6}$-alkyl, $C_{2-6}$-alkenyl, $C_{2-6}$-alkynyl, $C_{1-6}$-alkoxy, optionally substituted aryloxy or optionally substituted aryl. In some embodiments the acyl protection group is isobuturyl (—C(O=)CH(CH$_3$)$_2$) (also referred to herein as iBu). The term isobuturyl may also be spelt isobutyryl.

LNA Nucleoside

The LNA nucleoside of formula A and C, or as illustrated in formula B and D, is an oxy-LNA nucleoside, where the 2'-4' biradical is 2'-O—CH$_2$-4'. In some embodiments the oxy-LNA bridge is in the beta-D configuration (as illustrated in Formula A). In some embodiments the oxy-LNA bridge is in the alpha-L configuration (as illustrated in Formula C).

LNA Oligonucleotide

An LNA oligonucleotide is an oligonucleotide which comprises at least one LNA nucleoside. The LNA oligonucleotide may be an antisense oligonucleotide. The oligonucleotide present in Formula A, B, C or D is an LNA oligonucleotide as, at least the 3'-nucleotide is an LNA nucleotide. In some embodiments the two 3' most (3' terminal) nucleosides are LNA nucleosides, such as two 3' terminal beta-D-oxy LNA nucleosides.

The term oligonucleotide as used herein is defined as it is generally understood by the skilled person as a molecule comprising two or more covalently linked nucleosides. For use as an antisense oligonucleotide, oligonucleotides are typically synthesised as 7-30 nucleotides in length.

The LNA oligonucleotide may be of a design suitable for antisense oligonucleotides, for example a gapmer, a headmer, tailmer, a totalmer (fully LNA), or a mixmer (alternating regions of LNA and non-LNA nucleotides, such as LNA/DNA mixmers.

The term "antisense oligonucleotide" as used herein refers to oligonucleotides capable of modulating expression of a target gene by hybridizing to a target nucleic acid, in particular to a contiguous sequence on a target nucleic acid. An antisense oligonucleotide can also be defined by it's complementary to a target nucleic acid. Antisense oligonucleotides are single stranded. Antisense oligonucleotides are not essentially double stranded and are not therefore siRNAs. An antisense oligonucleotide comprises a contiguous nucleotide which is complementary to a target nucleic acid. Antisense oligonucleotides typically comprise one or more modified internucleoside linkages, and may by way of a non-limiting example be in the form of a LNA gapmer or a mixed wing gapmer. In other embodiments the oligonucleotide may be an LNA mixmers (LNA and non-LNA nucleotides, e.g. LNA and DNA (see e.g. WO2007/112754 hereby incorporated by reference), or LNA and 2'-O-MOE nucleotides, or LNA, DNA and 2'O-MOE nucleotides), or a LNA totalmers (only LNA nucleotides—see. E.g. WO2009/043353 hereby incorporated by reference).

Nucleobase

The term nucleobase, also referred to as "Base" herein, includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Nucleotides and Nucleosides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Modified nucleosides and nucleotides are modified as compared to the equivalent DNA or RNA nucleoside/tide by the introduction of a modification to the ribose sugar moiety, the nucleobase moiety, or the internucleoside linkage. Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety.

The term modified nucleoside may also be used herein interchangeably with the term "nucleoside analogue" or modified "units" or modified "monomers". Examples of modified nucleosides are described in the separate section "Oligomer modifications" and its sub-sections.

Modified Internucleoside Linkage

In some embodiments, the LNA oligonucleotide of Formula A or C comprises one or more modified internucleoside linkages.

The term "modified internucleoside linkage" is defined as generally understood by the skilled person as linkages other than phosphodiester (PO) linkages, that covalently couples two nucleosides together. Modified internucleoside linkages are particularly useful in stabilizing oligonucleotides for in vivo use, and may serve to protect against nuclease cleavage. A phosphorothioate internucleoside linkage is particularly useful due to nuclease resistance, beneficial pharmakokinetics and ease of manufacture. In some embodiments at least 70%, such as at least 80 or such as at least 90% of the internucleoside linkages in the oligonucleotide, or contiguous nucleotide sequence thereof, are phosphorothioate. Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

In some embodiments all of the internucleoside linkages of the oligonucleotide, or contiguous nucleotide sequence thereof, are phosphorothioate.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR"—CO—O—, —NR$^H$—CO—NR$^H$—, and/or the internucleoside linker may be selected form the group consisting of: —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C$_{1-4}$-alkyl.

The oligonucleotide may comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the oligonucleotide are phosphorothioate and/or boranophosphate linkages. Preferably, all the internucleoside linkages in the oligonucleotide are phosphorothioate linkages.

In some embodiments, the oligonucleotide is a phosphorothioate oligonucleotide. In some embodiments all internucleoside linkages in the oligonucleotide are phosphorothioate internucleoside linkages. In some embodiments the nucleoside linkages of the oligomer are independently selected from phosphodiester and phosphorothioate internucleotide linkages.

In some embodiments, the oligonucleotide comprises one or more affinity enhancing nucleosides, such as LNA or 2' substituted nucleosides described herein. Affinity enhancing nucleosides, such as 2'-O-MOE or 2'-O-methyl are often used in antisense oligonucleotides, either in combination with other nucleosides, such as DNA nucleosides, in the form of, e.g. mixmers or gapmers, or may be used in fully sugar modified oligonucleotides, where all of the nucleosides are other than DNA or RNA.

In some embodiments the oligonucleotide synthesised by the process or method of the invention may be a gapmer, an LNA gapmer, or a mixed wing gapmer.

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks are missing, i.e. only one of the ends of the oligonucleotide comprises affinity enhancing modified nucleosides. For headmers the 3' flank is missing (i.e. the 5' flank comprise affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-DNA, arabino nucleic acid (ANA) and 2'-fluoro-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Length

When referring to the length of a nucleotide molecule as referred to herein, the length corresponds to the number of monomer units, i.e. nucleotides, irrespective as to whether those monomer units are nucleotides or nucleotide analogues. With respect to nucleotides, the terms monomer and unit are used interchangeably herein.

The process of the present invention is particularly suitable for the purification of short oligonucleotides, for example, consisting of 7 to 30 nucleotides, such as 7-10, such as 7, 8, 9, 10 or 10 to 20 nucleotides, such as 12 to 18 nucleotides, for example, 12, 13, 14, 15, 16, 17 or 18 nucleotides.

Cleavage from the Solid Support

The oligonucleotide synthesized by the method of the invention is an LNA oligonucleotide comprising a 3' terminal LNA nucleoside. As shown in the examples, the present inventors have discovered that LNA oligonucleotides with a 3' terminal LNA bound to the solid support (e.g. a support containing a UnyLinker moiety, as disclosed herein), can be cleaved from the Unylinker moiety of the solid support under conditions for global deprotection and cleavage in about 30 minutes to about 6 hours using concentrated ammonium hydroxide solution at a temperature of about room temperature (about 20° C.) to about 60° C., or about 50° C. to about 60° C. Indeed within about 30 minutes to about 4 hours of global deprotection, LNA oligonucleotides with a 3' LNA nucleoside can be effectively cleaved and deprotected from a UnyLinker solid support. As illustrated in the examples, the present invention allows for effective cleavage and deprotection to be performed at room temperature within about 4 hours.

In some embodiments, the invention provides a method for the cleavage of an oligonucleotide from a solid support, said method comprising the step (i) of treating the oligonucleotide bound to the solid support with a concentrated ammonium hydroxide solution for a period of at least about 30 minutes and no longer than about 6 hours, wherein the 3' nucleoside of the oligonucleotide attached to the solid support is a LNA nucleoside, which is covalently attached to the solid support at the 3' position as according to formula A or C:

wherein the dark circle represents a solid support; $R^c$ is H or cyanoethyl; $R^e$ is aryl or $C_{1-10}$ alkyl, such as phenyl, isopropyl or methyl; wherein Base is a nucleobase, $R^3$ is the remainder of the oligonucleotide, and wherein X is O or S.

In some embodiments, the cleavage of the oligonucleotide from the solid support is performed at a temperature of about room temperature (about 20° C.) to about 60° C., or about 50° C. to about 60° C.

In some embodiments, at least about 90% of the oligonucleotide bound to the solid support are cleavage from the solid support in the method of the invention, i.e. effective cleavage, such as at least about 95%, such as at least about 98%, such as at least about 99%. In some embodiments, essentially all the LNA oligonucleotide bound to the solid support is cleaved during the method of the invention.

In some embodiments $R^e$ is methyl. In some embodiments $R^e$ is phenyl. In some embodiments $R^e$ is isopropyl.

In some embodiments the solid support is a polystyrene support (e.g. porous and polydispersed divinylbenzene cross-linked polystyrene particles). In some embodiments the solid support is a glass support (e.g. a controlled glass pore support). In some embodiments the solid support is a combination of polystyrene and glass supports. Solid supports (also called resins) are the insoluble particles, typically 50-200 μm in diameter, to which the oligonucleotide is bound during synthesis. Many types of solid support have been used, but controlled pore glass (CPG) and polystyrene or combinations hereof are most commonly used. Examples of such solid supports include 500 Å CPG, 1000 Å CPG, Kinnovate Nittophase®, Primer Support 5G, Prime Synthesis hybCPG™.

In some embodiments, the step of treating the oligonucleotide bound to the solid support with the ammonium hydroxide solution is for a period of at least about 30 minutes and no longer than about 5 hours.

In some embodiments, the step of treating the oligonucleotide bound to the solid support with the ammonium hydroxide solution is for a period of at least about 30 minutes and no longer than about 4 hours.

In some embodiments, the step of treating the oligonucleotide bound to the solid support with the ammonium hydroxide solution is for a period of at least about 30 minutes and no longer than about 3 hours.

In some embodiments, the step of treating the oligonucleotide bound to the solid support with the ammonium hydroxide solution is for a period of at least about 30 minutes and no longer than about 2 hours.

In some embodiments, the step of treating the oligonucleotide bound to the solid support with the ammonium hydroxide solution is for a period of at least about 30 minutes and no longer than about 90 minutes.

In some embodiments, the step of treating the oligonucleotide bound to the solid support with the ammonium hydroxide solution is for a period of at least about 45 minutes and no longer than about 5 hours.

In some embodiments, the step of treating the oligonucleotide bound to the solid support with the ammonium hydroxide solution is for a period of at least about 45 minutes and no longer than about 4 hours.

In some embodiments, the step of treating the oligonucleotide bound to the solid support with the ammonium hydroxide solution is for a period of at least about 45 minutes and no longer than about 3 hours.

In some embodiments, the step of treating the oligonucleotide bound to the solid support with the ammonium hydroxide solution is for a period of at least about 45 minutes and no longer than about 2 hours.

In some embodiments, the step of treating the oligonucleotide bound to the solid support with the ammonium hydroxide solution is for a period of at least about 45 minutes and no longer than about 90 minutes.

In some embodiments, the step of treating the oligonucleotide bound to the solid support with the ammonium hydroxide solution is for a period of at least about 60 minutes and no longer than about 5 hours.

In some embodiments, the step of treating the oligonucleotide bound to the solid support with the ammonium hydroxide solution is for a period of at least about 60 minutes and no longer than about 4 hours.

In some embodiments, the step of treating the oligonucleotide bound to the solid support with the ammonium hydroxide solution is for a period of at least about 60 minutes and no longer than about 3 hours.

In some embodiments, the step of treating the oligonucleotide bound to the solid support with the ammonium hydroxide solution is for a period of at least about 60 minutes and no longer than about 2 hours.

In some embodiments, the step of treating the oligonucleotide bound to the solid support with the ammonium hydroxide solution is for a period of at least about 60 minutes and no longer than about 90 minutes.

In some embodiments, the step of treating the oligonucleotide bound to the solid support with the ammonium hydroxide solution is for a period of at least about 90 minutes and no longer than about 5 hours.

In some embodiments, the step of treating the oligonucleotide bound to the solid support with the ammonium hydroxide solution is for a period of at least about 90 minutes and no longer than about 4 hours.

In some embodiments, the step of treating the oligonucleotide bound to the solid support with the ammonium hydroxide solution is for a period of at least about 90 minutes and no longer than about 3 hours.

In some embodiments, the step of treating the oligonucleotide bound to the solid support with the ammonium hydroxide solution is for a period of at least about 90 minutes and no longer than about 2 hours.

In some embodiments, the step of treating the oligonucleotide bound to the solid support with the ammonium hydroxide solution is for a period of up to about 1 hour or is about 1 hour.

In some embodiments, the step of treating the oligonucleotide bound to the solid support with the ammonium hydroxide solution is for a period of up to about 90 minutes.

In some embodiments, the step of treating the oligonucleotide bound to the solid support with the ammonium hydroxide solution is for a period of up to about 120 minutes.

In the above time periods, the temperature of the cleavage step may be from about 20° C. to about 60° C. or from about 50° C. to about 60° C.

In some embodiments, the method of the invention results in both cleavage of the oligonucleotide and global deprotection of the oligonucleotide. As illustrated in the examples, depending on the protection groups used, global deprotection may occur within about 30 minutes, or for some protection groups, such as iBu protected guanine residues (where the exocyclic nitrogen of guanine is protected with a iBu protection group) a period of over 1 hour may be needed, such as about 90 minutes. As can be shown in the examples, efficient deprotection is achieved using the methods of the invention, such as at least 95%, such as at least 98% or at least 99% deprotection within 30 minutes (e.g. when DMF protected gunanine residues are used), or between 1 and 2 hours for oligonucleotides which comprise a iBu protected guanine residue.

In some embodiments, the ammonium hydroxide treatment is performed for at least about 70 minutes, such as at least about 80 minutes, such as at least about 90 minutes, such as at least about 100 minutes, such as at least about 110 minutes or at least about 120 minutes.

In some embodiments, such as when the ammonium hydroxide treatment is performed for at least 60 minutes or more, the LNA oligonucleotide comprises at least one acyl protected guanine residue. The acyl protected guanine may be on either a LNA nucleoside or a non LNA nucleoside, such as a DNA nucleoside.

In some embodiments, the LNA oligonucleotide bound to the solid support is treated with the ammonium hydroxide solution for a period of at least about 2 hours, wherein said step further results in global deprotection of the LNA oligonucleotide, wherein the LNA oligonucleotide comprises at least one acyl protected guanine residue.

In some embodiments, the LNA oligonucleotide does not comprises an acyl protected guanine residue or an iBu protected guanine residue. As illustrated in the examples, cleavage and deprotection of LNA oligonucleotides with guanine protection groups other than iBu or other than acyl, such as DMF protected gunanine residues, or oligonucleotides which do not comprise guanine residues, are very rapidly cleaved and deprotected, essentially with about 30 minutes-about 1 hour.

In some embodiments, all guanine residues present in the LNA oligonucleotide attached to the solid support are DMF protected guanine residues.

In some embodiments, the cleavage step (step (i)) is performed using concentrated ammonium hydroxide at about 55° C.-about 60° C.

In some embodiments, step (i) is performed using concentrated ammonium hydroxide at a temperature of about 55° C.

In some embodiments, the oligonucleotide is a phosphorothioate oligonucleotide of 10-25 nucleotides in length.

Oligonucleotide Synthesis Method

The invention provides for a method of oligonucleotide synthesis comprising the following steps:

a) Provision of a solid support of Formula B or D

Formula B beta-D-oxy LNA Nucleoside

Formula D

α-L-oxy LNA Nucleoside wherein the dark circle represents a solid support; $R^c$ is H or cyanoethyl; $R^e$ is aryl or $C_{1-10}$ alkyl, such as phenyl, isopropyl or methyl; wherein Base is a nucleobase, wherein X is O or S.

and Rz is a 5'-OH blocking group, such as a blocking group selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$ b) unblocking of the 5' group to provide a 5' terminal —OH group c) coupling a phosphoramidite monomer to the 5' terminal —OH group d) oxidizing the internucleoside linkage formed in the coupling step e) optionally capping any unreacted 5' terminal —OH group f) repeating steps c)-e) for one or more further cycles (chain elongation)

g) Optionally carrying out an amine wash h) Cleavage of the oligonucleotide from the solid support by the method of the invention, such as treatment of the oligonucleotide bound to the solid support with a concentrated ammonium hydroxide solution for a period of at least about 30 minutes and no longer than about 6 hours i) Optionally, purifying the cleaved oligonucleotide.

When steps c)-e) are repeated (further elongation cycles) (step f)—typically the next phosphoramidite monomer is provided in a form where the 5'-OH group is blocked (e.g. using a blocking group referred to in step a), and is deblocked prior to coupling.

In some embodiments, the blocking group referred to in step a) or present in the phosphoramidite monomer prior to coupling is —$CH_2$—O-DMTr.

In some embodiments, $R^z$ present in Formula B or D and on the phosphoramidite monomer used in step c) is —$CH_2$—O-DMTr.

The amine wash step refers to an optional procedure used in oligonucleotide synthesis wherein prior to exposure of the oligonucleotide to the strong basic conditions used in the cleavage step the oligonucleotide is treated with a solution of a weak base in an organic solvent, such as treatment with 10% diethylamine in acetontrile, or 1:1 triethylamine/acetonitrile. The amine wash results in the removal of the phosphate protection groups without cleavage of the oligonucleotide from the solid support. The benefit of including an amine wash results in the avoidance of unwanted cyanothyl adducts, such as acrylonitrile, which form due to a side reaction of the phosphate protection group ($R^c$), such as cyanoethyl protection group and heterocyclic bases, particularly thymine.

The purification step i) may use any suitable method for oligonucleotide purification such as ion exchange purification or reversed phase chromatography, or both ion exchange purification and reversed phase chromatography. In some embodiments purification comprises the sequential steps: a) ion exchange purification, b) desalting, e.g. via diafiltration, followed by c) lyophilisation and d) reversed phase chromatography. Prior to purification it is typical that the ammonium hydroxide is either removed or at least diluted.

In some embodiments, the purification step may comprise desalting, such as desalting by diafiltration or size-exclusion chromatography.

Alternatively, DMT-ON reversed phase purification followed by detritylation is also an option for purifying oligonucleotides (see Capaldi and Scozzari, Chapter 14, Antisense Drug Technology: Principles, Strategies, and Applications, CRC Press 2008.

In some embodiments the above method comprises both step (g) and (i).

In some embodiments the above method comprises steps (e) (g) and (i).

In some embodiments, steps b)-e) (the elongation cycle) is repeated between about 7-25 times, such as 8, 9, 10, 11, 12, 13, 14, 15, 16, 17, 18, 19, 20, 21, 22, 23 or 14 times.

Step b)—the deblocking step may comprise detritylation. For example, when the support-bound nucleoside has a 5'-DMT protecting group (DMT=4,4'-dimethoxytrityl), the role of which is to prevent polymerization during resin functionalization, and this protecting group must be removed (detritylation) from the support-bound nucleoside before oligonucleotide synthesis can proceed.

Coupling is typically performed in a suitable solvent such as acetonitrile and an activator. In some embodiments, the solvent comprises N-methylimidazole. In some embodiments, the solvent composition comprises N-methylimidazole in a concentration of 0.01-about 1M N-methylimidazole, such as about 0.1 M N-methylimidazole. In some embodiments, the activator comprises 4,5-dicyanoimidazole (DCI), tetrazole, or 5-(Benzylthio)-1H-tetrazole. In some embodiments, the solvent composition comprises about 0.5-about 2M DCI.

Coupling results in the production of a phosphite Wester intermediate, which is then oxidized in the next step, such as in the presence of iodine (resulting in a phosphodiester linkage) or a sulfurizing agent to produce a phosphorothioate linkage.

In some embodiments, the oxidation is a sulfurization step, which results in the production of a phosphorothioate linkage: Sulphurization may be performed by treatment with a sulphurizing reagent, such as 3H-1,2-Benzodithiol-3-one-1,1-dioxide or Phenyl acetyl disulfide, or Xanthane Hydride in a suitable solvent such as acetonitrile and optionally comprising an aromatic heterocyclic solvent such as pyridine, or 3-methylpyridine. In some embodiments, sulfurization is performed in 0.1M solution of xanthane hydride in acetonitrile and pyridine 1:1 v/v. Sulfurization is typically performed at room temperature. The optional capping step is useful in that whilst coupling yields may typically be around 99.5% during each coupling step, there may be a level of 99.5% unreacted 5'-OH groups on the resin bound nucleotide which if left would be available to the next round of coupling resulting in a n−1 impurity in the final oligonucleotide. "capping" step after the coupling reaction, to block the unreacted 5'-hydroxyl groups. Two capping solutions are used on the synthesizer: acetic anhydride and N-methylimidazole (NMI). These two reagents (dissolved in tetrahydrofuran and/or acetonitrile with the addition of a small quantity of pyridine) are mixed on the DNA synthesizer prior to delivery to the synthesis column. The electrophilic mixture rapidly acetylates alcohols, and the pyridine ensures that the pH remains basic to prevent undesired detritylation of the support bound oligonucleotide by the acetic acid formed by reaction of acetic anhydride with NMI. Acetylation of the 5'-hydroxyl groups renders them inert to subsequent reactions.

In some embodiments, when the oxidation is a sulfurization, capping is performed after the sulfurization step.

In some embodiments, the phoshoramidite monomer used in step c) is of formula E:

Formula E wherein $R^2$ is selected from the groups consisting of hydrogen, hydroxyl, halo, such as —F, amino, azido, —SH, —CN, —OCN, —CF$_3$, —OCF$_3$, —O($R_m$)-alkyl, —S($R_m$)-alkyl, —N($R_m$)-alkyl, —O($R_m$)-alkenyl, —S($R_m$)-alkenyl, —N($R_m$)-alkenyl; —O($R_m$)-alkynyl, —S($R_m$)-alkynyl or —N($R_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N($R_m$)($R_n$) or O—CH$_2$C(=O)—N($R_m$)($R_n$), —O—(CH$_2$)$_2$OCH$_3$, and —O—CH$_3$, where each $R_m$ and $R_n$ are independently, H, an amino protecting group or substituted or unsubstituted $C_{1-10}$ alkyl;

$R^4$= is selected from the group consisting of alkyl, cycloalkyl, cyclo-heteroalkyl, O-alkyl, S-alkyl, NH-alkyl, and hydrogen;

or, $R^4$ and $R^2$ together form a biradicale bridge between the C2' and C4' of the ribose ring of the nucleoside forming a bicyclic nucleic acid, also referred to as a locked nucleic acid (LNA). In some embodiments, the $R^2$-$R^4$ biradicle is either —O—CH$_2$— or —O—CH(CH$_3$)—.

wherein Rz is Rz is a 5'-OH blocking group, such as a blocking group selected from the group consisting of CH$_2$ODMTr, CH$_2$-Alkyl-O-DMTr, CH-Me-O-DMTr, CH$_2$OMMTr, CH$_2$-Alkyl-O-MMTr, and CH(Me)-O-MMTr.

In some embodiments, $R^z$ present in Formula AB or D and/or on the phosphormaidite monomer used in step c) is CH$_2$—O-DMTr.

In some embodiments, $R^4$ is hydrogen, and $R^2$ is selected from the group consisting of $C_{1-6}$ alkyl, methyl, $C_{2-6}$ alkoxy, 2'-O-methoxyethyl, amino, and fluoro.

In some embodiments, $R^4$ is hydrogen, and $R^2$ is hydrogen.

In some embodiments, $R^4$ is hydrogen, and $R^2$ is hydroxy.

In some embodiments, the LNA oligonucleotide is a phosphorothioate oligonucleotide, where the phosphorothioate internucleoside linkages are not stereocontrolled, i.e. are stereo-random.

EXAMPLES

Example 1

7×20 µmole scale synthesis was carried out using Kinnovate Unylinker polystyrene support with a loading (as measured by detritylation) of 200 µmol/g.

Figure 3:
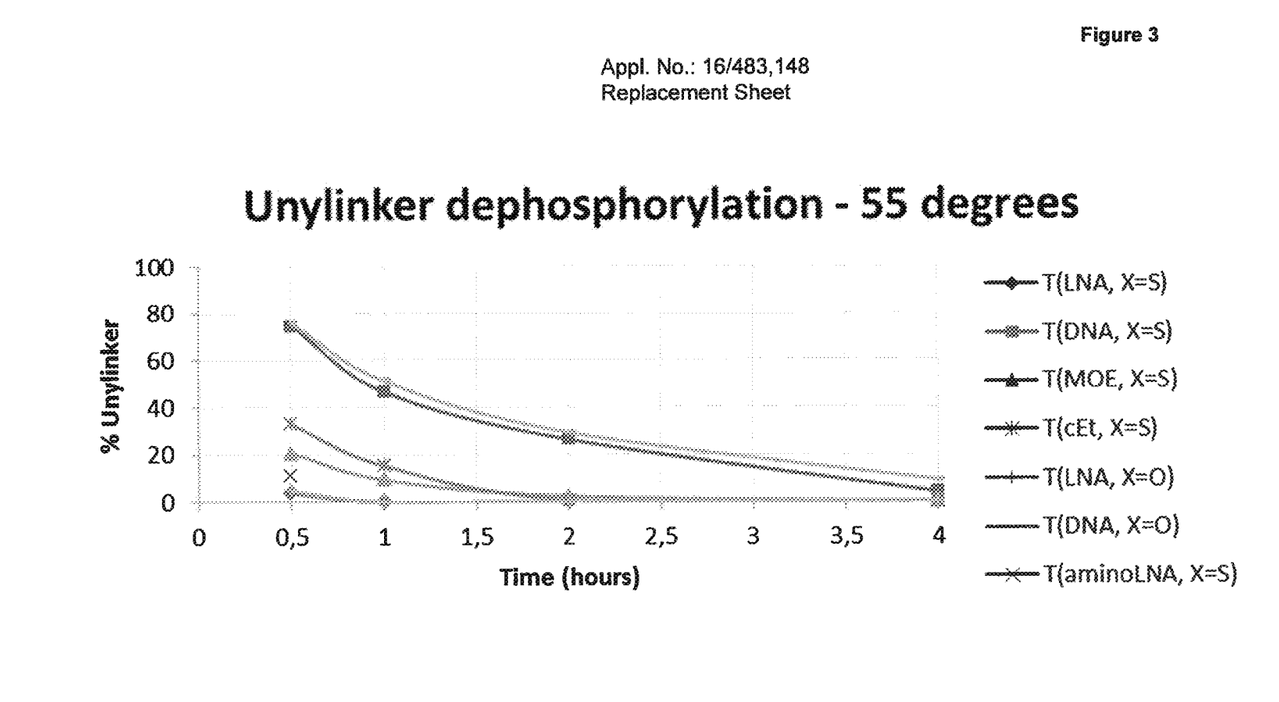
FIG. 3: Unylinker dephosphorylation rates in concentrated ammonium hydroxide at 55° C. from Example 1.

The following oligonucleotides were synthesized:

5'-[(dt)$_s$]$_{11}$T*-3'

Wherein T* indicated a T nucleoside, with the ribose moiety of the nucleoside is varied from the group consisting of 2'-deoxyribose (DNA), 2'-O-methoxyethyl ribose (2'-MOE), LNA, aminoLNA and (S)cEt, as indicated in FIG. 3. The linkage between the 3'-nucleoside and the Unylinker moiety of the solid support was varied from a phosphodiester linkage (X=O of formula A) or a phosphorthioate linkage (X=S of formula A), if indicated in FIG. 3. A total of 7 synthesis was therefore carried out.

The synthesis was carried out using conventional 5'-dimethoxytrityl-3'-β-cyanoethyl phosphoramidites, as shown in formula D-H

DNA

Formula D

LNA

Formula E

(S)cEt

Formula F

MOE

Formula G aminoLNA

Formula H

The synthesis was carried out with the following synthetic steps with the reagents listed below:
a) Deblocking the support bound ODMTr group providing a terminal —OH group using 3% Dichloroacetic acid in dichloromethane (v/v)
b) Coupling a phosphoramidite monomer of formula D-G (0.1M in Acetonitrile) to the terminal —OH group, using 0.5 M Dicyanoimidazole in acetonitrile as activator
c) oxidizing the internucleoside linkage formed in the coupling step with either 0.1M Xanthane hydride in 1:1

Acetonitrile and pyridine (X=S) or Pyridine/Water/Iodine 9/1/12.7 (v/v/w) (X=O)

d) Capping with a 2:1:1 mixture of Cap A, CapB1 and CapB2:

Cap A 20% 1-Methylimidazol in acetonitrile (v/v)
Cap B1 40% Acetic acid anhydride in acetonitrile (v/v)
Cap B2 60% Pyridine or 2,6-lutidine in acetonitrile (v/v)

repeating steps a)-d) for one or more further cycles (chain elongation).

The synthesis was carried out DMT-Off, meaning that at the end of the chain elongation, step a) was carried out to cleave the final 5'-DMTr Group. Hereafter the support bound oligonucleotide was treated with a solution of Diethylamine in acetonitrile (20% V/V) for 1 h.

Figure 1:
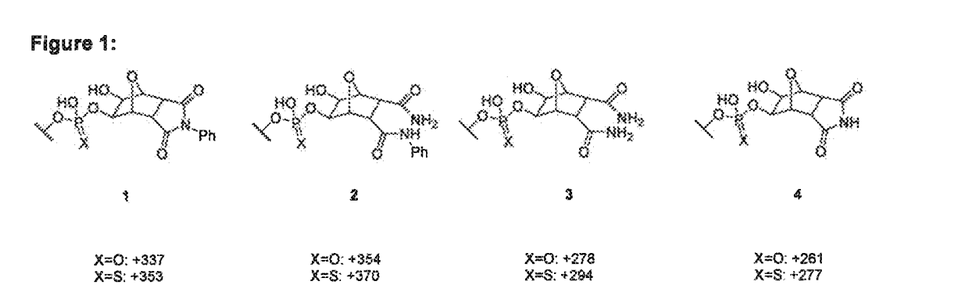
FIG. 1: Theoretical species observed upon incomplete Unylinker dephosphorylation together with the increase in mass, that will be observed if this species is present as a consequence of incomplete dephosphorylation.

1/10 of the resulting solid support was hereafter mixed with 1 mL concentrated ammonium hydroxide, and left for 0.5-4 h at 55° C., as indicated in FIG. 1, followed by evaporation in vacuo, and analysis by reversed phase UPLC-MS.

Figure 2:
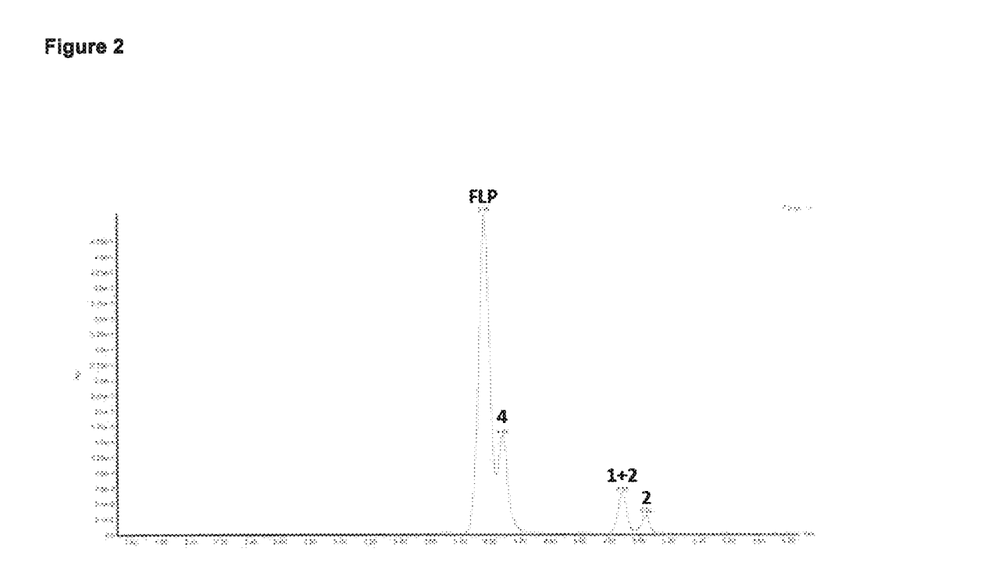
FIG. 2: Example of a chromatogram from example 1, wherein 3 of the species from FIG. 1 is observed, as indicated with compound numbers 1-4. FLP means "Full length product", which is the desired dephosphorylated oligonucleotide.

In all cases, the % Unylinker is calculated as the sum of 3 peaks found originating from incomplete dephosphorylation, according to FIG. 2. All peaks are detected via absorbance at 260 nm.

Results are shown in the table below, and in FIG. 3.

TABLE 1

Percent unylinker found as a function of deprotection time at 55° C. for the indicated ribose modifications, and linkages between the 3'-nucleoside and the Unylinker moiety.

| time (h) | 0.5 | 1 | 2 | 4 |
|---|---|---|---|---|
| T(LNA, X = S) | 3.83 | 0 | 0 | 0 |
| T(LNA, X = O) | 4.84 | 0 | 0.24 | 0 |
| T(DNA, X = S) | 74.69 | 46.6 | 26.24 | 4.04 |
| T(DNA, X = O) | 76.05 | 51.23 | 29.19 | 9.09 |
| T(MOE, X = S) | 20.58 | 9.4 | 2.44 | 0 |
| T(cEt, X = S) | 32.77 | 15.27 | 0.94 | 0 |
| T(aminoLNA, X = S) | 11.34 | 9.37 | 2.63 | 0 |

Example 2

7×20 µmole scale synthesis was carried out using Kinnovate Unylinker polystyrene support with a loading (as measured by detritylation) of 200 µmol/g.

Figure 4:
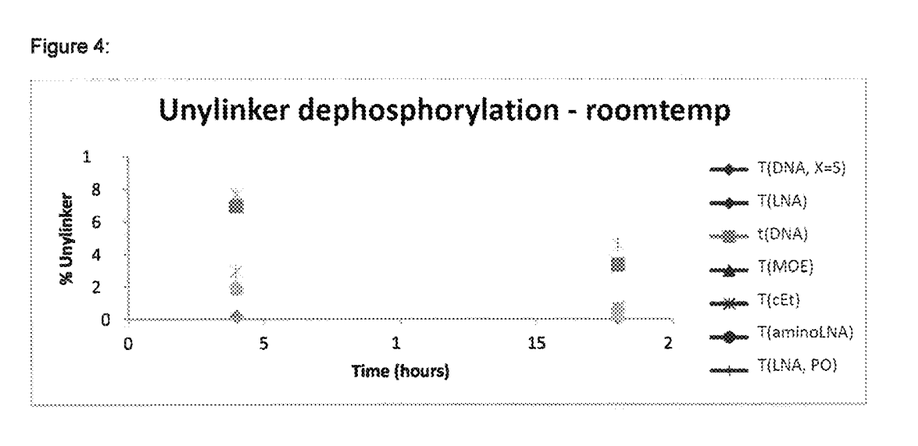
FIG. 4: Unylinker dephosphorylation rates in concentrated ammonium hydroxide at room temperature from Example 2.

The following oligonucleotides were synthesized:

5'-[(dt)$_s$]$_{11}$T*-3'

Wherein T* indicated a T nucleoside, with the ribose moiety of the nucleoside is varied from the group consisting of 2'-deoxyribose (DNA), 2'-O-methoxyethyl ribose (2'-MOE), LNA, aminoLNA and (S)cEt, as indicated in FIG. 4. The linkage between the 3'-nucleoside and the Unylinker moiety of the solid support was varied from a phosphodiester linkage (X=O of formula A) or a phosphorthioate linkage (X=S of formula A), if indicated in FIG. 4. A total of 7 synthesis was therefore carried out.

The synthesis was carried out using conventional 5'-dimethoxytrityl-3'-β-cyanoethyl phosphoramidites, as shown in formula D-H in example 1.

The synthesis was carried out with the following synthetic steps with the reagents listed below:

a) Deblocking the support bound ODMTr group providing a terminal —OH group using 3% Dichloroacetic acid in dichloromethane (v/v)
b) Coupling a phosphoramidite monomer of formula D-G (0.1M in Acetonitrile) to the terminal —OH group, using 0.5 M Dicyanoimidazole in acetonitrile as activator
c) oxidizing the internucleoside linkage formed in the coupling step with either 0.1M Xanthane hydride in 1:1 Acetonitrile and pyridine (X=S) or Pyridine/Water/Iodine 9/1/12.7 (v/v/w) (X=O)
d) Capping with a 2:1:1 mixture of Cap A, CapB1 and CapB2:

| Cap A | 20% 1-Methylimidazol in acetonitrile (v/v) |
|---|---|
| Cap B1 | 40% Acetic acid anhydride in acetonitrile (v/v) |
| Cap B2 | 60% Pyridine or 2,6-lutidine in acetonitrile (v/v) | repeating steps a)-d) for one or more further cycles (chain elongation).

The synthesis was carried out DMT-Off, meaning that at the end of the chain elongation, step a) was carried out to cleave the final 5'-DMTr Group. Hereafter the support bound oligonucleotide was treated with a solution of Diethylamine in acetonitrile (20% V/V) for 1 h. 1/10 of the resulting solid support was hereafter mixed with 1 mL concentrated ammonium hydroxide, and left for 4 or 18 hours at room temperature, as indicated in FIG. 1, followed by evaporation in vacuo, and analysis by reversed phase UPLC-MS.

In all cases, the % Unylinker is calculated as the sum of 3 peaks found originating from incomplete dephosphorylation, according to FIG. 2. All peaks are detected via absorbance at 260 nm.

Results are shown in table 2 below, and in FIG. 4.

TABLE 2

Percent unylinker found as a function of deprotection time at room temperature for the indicated ribose modifications, and linkages between the 3'-nucleoside and the Unylinker moiety.

| time (h) | 4 | 18 |
|---|---|---|
| T(LNA, X = S) | 1.75 | 0.3 |
| T(LNA, X = O) | 0.84 | 0.27 |
| T(DNA, X = S) | 69.8 | 33.32 |
| T(DNA, X = O) | 77.03 | 45.76 |
| T(MOE, X = S) | 20.1 | 2.56 |
| T(cEt, X = S) | 29.69 | 6.66 |
| T(aminoLNA, X = S) | 18.66 | 5.79 |

The invention claimed is:

1. A method for the cleavage of an oligonucleotide from a solid support, said method comprising the step (i) of treating the oligonucleotide bound to the solid support with a concentrated ammonium hydroxide solution for a period of at least about 30 minutes and no longer than about 2 hours at a temperature ranging from about 50° C. to about 60° C., wherein the 3' nucleoside of the oligonucleotide attached to the solid support is a LNA nucleoside, which is covalently attached to the solid support at the 3' position as according to Formula I or II Formula I — beta-D-oxy LNA Nucleoside Formula II — α-L-oxy LNA Nucleoside Formula A — beta-D-oxy LNA Nucleoside Formula C — α-L-oxy LNA Nucleoside wherein one of A' and A" is SM or L-SM, SM is a support medium;

L is a linking moiety;

the other of A' and A" is H or a substituent;

each of $R_u$, $R_v$, $R_w$, $R_x$, $R_y$, and $R_z$ is H, alkyl, substituted alkyl, alkenyl, substituted alkenyl, alkynyl or substituted alkynyl;

$Y_1$ and $Y_2$ are each independently of one another O, S, $NR_1CH_2$ or $CR_1R_1$: $R_1$ is H, alkyl, substituted alkyl, alkenyl, substituted alkenyl, alkynyl or substituted alkynyl;

$G_1$ is O, S, or NR'; wherein R' is H or a substituent,

X is O or S, $R^c$ is H or cyanoethyl;

Base is a nucleobase; and $R^3$ is the remainder of the oligonucleotide; and substituents are independently selected from $C_{1-4}$ alkyl group, $C_{6-14}$ aryl group, $C_{1-4}$ alkoxy group, $C_{7-14}$ aralkyl group, $C_{1-4}$ alkyl, and halo.

2. The method according to claim 1, wherein the 3' nucleoside of the oligonucleotide attached to the solid support is a LNA nucleoside, which is covalently attached to the solid support at the 3' position according to Formula A or C:

wherein the filled circle represents a solid support; X is O or S, $R^c$ is H or cyanoethyl; $R^e$ is aryl or $C_{1-10}$ alkyl; wherein Base is a nucleobase, $R^3$ is the remainder of the oligonucleotide.

3. The method according to claim 1 or 2, wherein the 3' nucleoside of the oligonucleotide attached to the solid support is a LNA nucleoside, which is covalently attached to the solid support at the 3' position according to Formula I or Formula A.

4. The method according to claim 1 or 2, wherein the 3' nucleoside of the oligonucleotide attached to the solid support is a LNA nucleoside, which is covalently attached to the solid support at the 3' position according to Formula II or Formula C.

5. The method according to claim 1, wherein one of A" or A' is methyl, isopropyl or phenyl.

6. The method according to claim 1, wherein $R^c$ is cyanoethyl.

7. The method according to claim 1, wherein X is O.

8. The method according to claim 1, wherein X is S.

9. The method according to claim 1, wherein the step of treating the oligonucleotide bound to the solid support with the ammonium hydroxide solution is for a period of up to about 1 hour or is about 1 hour.

10. The method according to claim 1, further comprising wherein the step of treating the oligonucleotide bound to the solid support with the ammonium hydroxide solution is for a period of at least about 2 hours, wherein said step further results in global deprotection of the LNA oligonucleotide, and wherein the oligonucleotide comprises at least one acyl protected guanine residue.

11. The method according to claim 1, further comprising wherein the LNA oligonucleotide does not comprises an acyl protected guanine residue or does not comprise an iBu protected guanine residue.

12. The method according to claim 1, further comprising wherein all guanine residues present in the LNA oligonucleotide are DMF protected guanine residues.

13. The method according to claim 1, further comprising wherein the oligonucleotide is a phosphorothioate oligonucleotide of 10-25 nucleotides in length.

14. A method of oligonucleotide synthesis comprising the following steps:

a) providing a solid support of according to Formula B or D

Formula B beta-D-oxy LNA Nucleoside

Formula D

α-L-oxy LNA Nucleoside wherein,
the filled circle represents a solid support,
$R^c$ is H or cyanoethyl,
Base is a nucleobase,
$R^c$ is H or cyanoethyl,
$R^e$ is aryl or $C_{1-10}$ alkyl,
and $R^z$ is a 5'-OH blocking group selected from the group consisting of $CH_2O$ dimethoxytrityl, $CH_2$-alkylenyl-O-dimethoxytrityl, CH-Me-O-dimethoxytrityl, $CH_2O$ monomethoxytrityl, $CH_2$-Alkyl-O-monomethoxytrityl, and CH(Me)-O-monomethoxytrityl;

a) unblocking of the 5' group by acid hydrolysis of the 5' trityl-type protecting group to provide a 5' terminal —OH group;
b) coupling an appropriately protected nucleoside phosphoramidite monomer to the 5'terminal —OH group;
c) oxidizing or sulfurizing the internucleoside linkage formed in the coupling step;
d) optionally capping any uncoupled phosphoramidite monomers;
e) repeating steps b)-e) for one or more further cycles (chain elongation);
f) optionally carrying out an amine wash treatment;
g) cleaving the oligonucleotide from the solid support by treating the oligonucleotide bound to the solid support with a concentrated ammonium hydroxide solution for a period of at least about 30 minutes and no longer than about 2 hours at a temperature ranging from about 50° to about 60° C.; and
h) optionally purifying the oligonucleotide.

* * * * *